United States Patent [19]

Sheridan et al.

[11] 3,996,939
[45] Dec. 14, 1976

[54] INTUBATION STYLETS
[75] Inventors: David S. Sheridan, Argyle; Isaac S. Jackson, Greenwich, both of N.Y.
[73] Assignee: National Catheter Corporation, Argyle, N.Y.
[22] Filed: July 22, 1975
[21] Appl. No.: 597,999
[52] U.S. Cl. .......................... 128/351; 128/DIG. 9
[51] Int. Cl.² ........................................ A61M 25/00
[58] Field of Search .......................... 128/348–351, 128/341, 343, 2 M, 2.05 R, DIG. 9

[56] References Cited
UNITED STATES PATENTS

| | | | |
|---|---|---|---|
| 229,633 | 7/1880 | Pfarre | 128/341 |
| 2,541,402 | 2/1951 | Caine | 128/351 |
| 2,670,539 | 3/1954 | Wall | 32/33 |
| 3,169,528 | 2/1965 | Knox et al. | 128/276 X |
| 3,508,554 | 4/1970 | Sheridan | 128/348 |
| 3,757,768 | 9/1973 | Kline | 128/2 M |
| 3,802,440 | 4/1974 | Salem et al. | 128/351 |
| 3,957,055 | 5/1976 | Linder et al. | 128/351 |

OTHER PUBLICATIONS

Jo. Amer. Soc. Anest., Inc., Mar.–Apr., 1968, vol. 29, No. 2. p. 385.

*Primary Examiner*—Dalton L. Truluck
*Attorney, Agent, or Firm*—Carroll F. Palmer

[57] ABSTRACT

A stylet for use in intubating an endotracheal tube, catheter or like medico-surgical tube comprises a bendable metal rod hermetically sealed in a tubular plastic sheath so the rod is closely encircled by the sheath, but so the two can flex longitudinally independently of each other. The ends of the sheath are molded in a smoothly rounded closed shape and it has a frosted finish on its external surface.

4 Claims, 6 Drawing Figures

INTUBATION STYLETS

BACKGROUND OF THE INVENTION

1. Field of the Invention

This invention relates to improvements in stylets that are used for intubating an endotracheal tube, catheter or like medico-surgical tube in a patient.

2. Description of the Prior Art

The use of a stylet in a catheter or tube for the purpose of stiffening or shaping, is an accepted practice for introducing or intubating a patient. In the past stylets made from music wire, malleable copper wire, plastic rods, etc., have been used (see U.S. Pat. No. 3,460,541). Wire has the desirable characteristics for stiffness and shaping. However, on occasions the wire, through accidents, has become a trauma causing instrument. A plastic stylet cannot be as readily shaped and therefore is not generally acceptable.

Intubation stylets of more complicated structure than a mere wire or rod have been developed (see U.S. Pat. No. 2,463,149). Such stylets include tubular metal devices with articulated end units (see U.S. Pat. Nos. 2,541,402 and 3,314,431). Although these stylets may be quite effective in use, they are so expensive to make, they cannot be marketed as single-use disposable items. Hence, they are not compatible with the current trend in marketing and use of medico-surgical tube devices of the single-use disposable type.

OBJECTS

A principle object of this invention is the provision of intubation stylets of improved form.

A further object is the provision of intubation stylets that can be made and sold as single-use disposable items.

Another object is the provision of such stylets having the desired qualities of stiffness and shapability, but which are structured so as to avoid the possibility of causing trauma to a patient during intubation use.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The foregoing objects are accomplished according to the invention by the provision of intubating stylets that comprise a metal rod having a proximal end and a distal end encased in a tubular sheath made of waterproof, non-fibrous plastic material. The sheath has an I.D. slightly larger than the O.D. of the rod and the two are not permanently affixed to one another so that they may move relative to each other and they may flex longitudinally independently of each other.

The rod has a loop in its proximal end and is made of such metal or metal alloy that it is capable of being bent into a desired configuration and will remain in such shape.

The sheath has a frosted finish on its external surface and its ends are smoothly rounded and fused closed so the rod is hermetically sealed within the sheath.

BRIEF DESCRIPTION OF THE DRAWINGS

A more complete understanding of the improved intubation stylets of the invention may be obtained by reference to the accompanying drawings in which.

DESCRIPTION OF PREFERRED EMBODIMENTS

Figure 1:
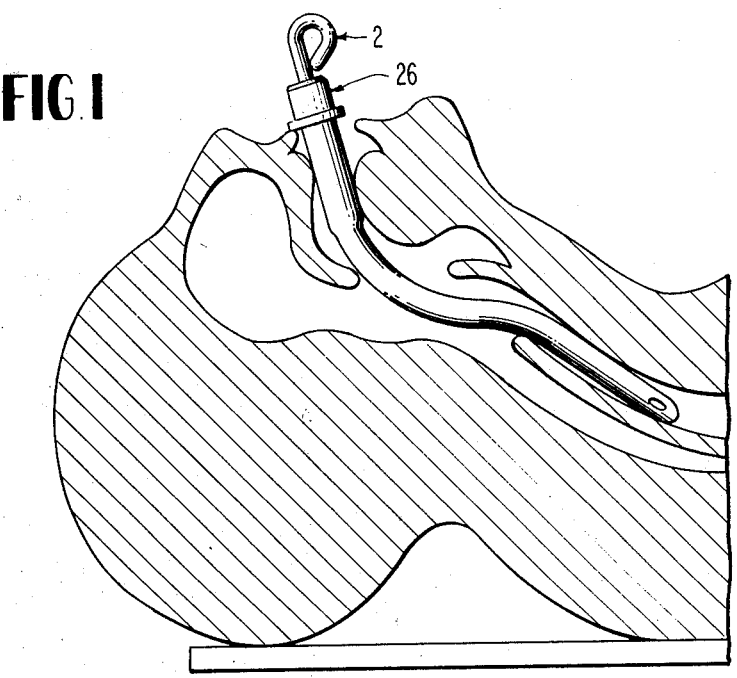
FIG. 1 is a diagramatic view, partly in section, of an endotracheal tube being intubated into a patient using a stylet of the invention to assist in the passage and placement of the tube.

Referring in detail to the drawings, the stylet 2 comprises a metal rod 4 having a distal end 6 and a proximal end 8. A loop 10 is formed in the proximal end.

A tubular sheath 12 of waterproof, non-fibrous plastic material encases the metal rod 4 with the inside surface 14 of the sheath spaced apart, but close to the outside surface 16 of the rod, e.g., the space 18 between the sheath I.D. and the rod O.D. will be about 0.01 - 1mm. There are no permanent connections between the rod 4 and sheath 12 so they can move longitudinally relative to one another.

The sheath 12 is slightly longer, e.g., by about 1 – 15 mm., than the rod 4 so the distal end 20 and proximal end 22 of the sheath each extend beyond the corresponding ends of the rod. The sheath ends 20 and 22 are both molded under heat to have a smoothly rounded, closed shape that hermetically seals the rod 4 in the sheath 12. The exterior surface 24 of the sheath 12 has a frosted surface such as described in U.S. Pat. No. 3,508,554, the disclosure of which is incorporated herein by reference as to the description of such surface and method of its formation.

The tubular sheath may be formed of a variety of flexible, waterproof, non-fibrous plastic materials, e.g., polyethylene, nylon, ethylene-propylene copolymer or the like. Advantageously, the sheath is made of plasticized polyvinyl chloride resin formulated to have a Shore A durometer rating between about 70 to 85.

The rod 4 is preferrably made of aluminum metal or aluminum alloy, particularly a soft variety such as type 1100-0. However, the rod may be made of other metals or alloys, e.g., copper, bronze, monel, stainless steel, magnesium, etc., in a diameter relative to the metal hardness and ductility to approximate the same stiffness and bendability properties as a rod made of said type 1100-0 aluminum. As an example, in a stylet of the invention designed for use with a 32 French size endotracheal tube the length will be 38 cm. from end 20 to end 22, the loop 10 has a radius of about 1 cm., the rod 4 has an O.D. of 3.0 mm., sheath 12 has an O.D. of 4.5 mm. and an I.D. of 3.1mm. The endotracheal tubes 26 with which the stylets 2 are used will vary in size, e.g., from pediatric size 12Fr. (I.D. size 3.0 mm.) to 40Fr. (I.D. size 10.0 mm) and may be with or without balloon cuffs, e.g., Murphy type, Magill type, etc. (see U.S. Pat Nos. 3,605,750 and 3,625,793). These various size tubes are, of course, of different lengths and the stylets of the invention will need to be varied in size to correspond with the endotracheal tubes, catheters or the like with which they are designed to be used.

Figure 2:
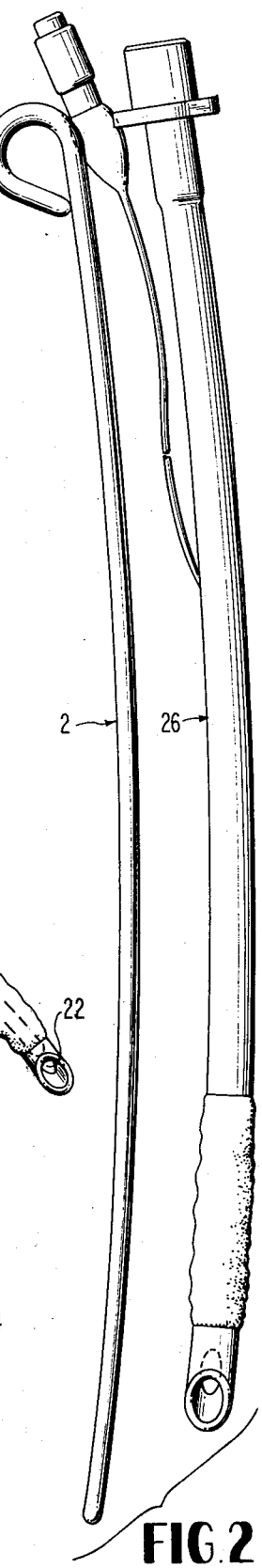
FIG. 2 is a plan view of an intubation stylet of the invention beside an endotracheal tube in which it may be used as illustrated in FIG. 1.
Figure 3:
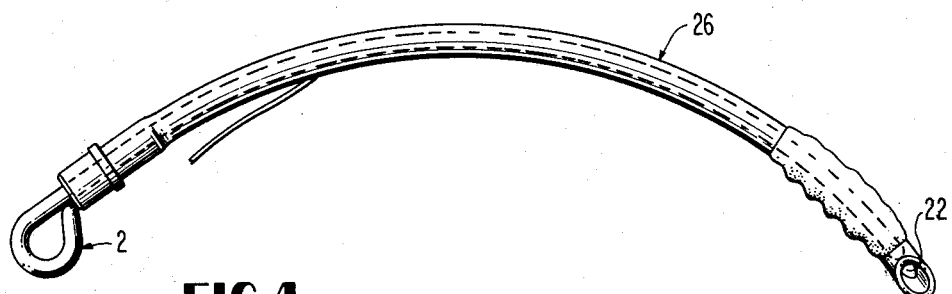
FIG. 3 is a plan view showing the stylet of FIG. 2 positioned within a endotracheal tube in position for use.
Figure 4:
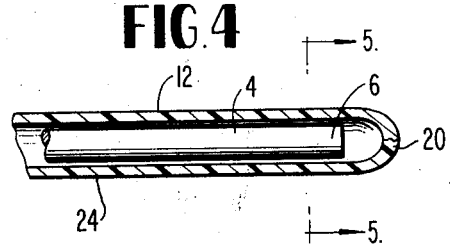
FIG. 4 is an enlarged, fragmentary view, partially in section, of the distal end portion of the stylet.
Figure 5:
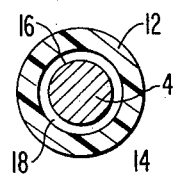
FIG. 5 is an enlarged sectional view taken on the line 5—5 of FIG. 4.
Figure 6:
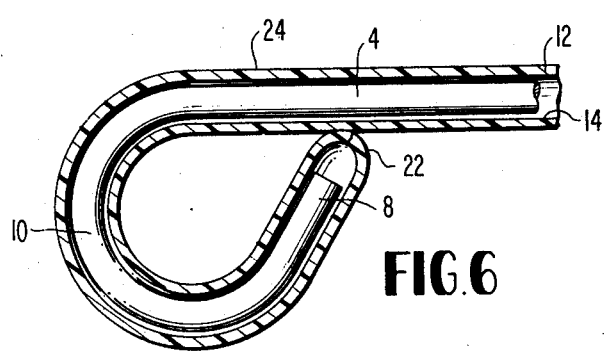
FIG. 6 is an enlarged, fragmentary view, partially in section, of the proximal end portion of the stylet.

For use the stylet 2 separated from the endotube 26 as seen in FIG. 2, is inserted into the endotube as shown in FIG. 3. As so positioned, the stylet can be bent into a wide choice of complex shapes and will impart such shape to the endotube (see FIG. 1) and hold the endotube in such configuration until the intubation is completed. At that point, the stylet is withdrawn from the endotube. Such withdrawal is easily accomplished being assisted by the fact that there is no "grabbing" of the stylet by the inner surface of the endotube because of the frosted finish on the exterior of the stylet.

The embodiments of the invention in which an exclusive property or privilege is claimed are defined as follows:

1. A stylet for use in intubating an endotracheal tube comprising:
   a metal rod having a distal end and a proximal end, said rod being capable of being bent into a desired configuration and remaining in such configuration,
   a loop in said rod at the proximal end thereof,
   a tubular sheath of flexible waterproof, nonfibrous plastic material encasing said rod, said sheath having an inside diameter slightly larger than the outside diameter of said rod, said rod being moveable relative to said sheath,
   said sheath being slightly longer than said rod,
   the ends of the sheath being molded in a smoothly rounded, closed shape hermetically sealing the rod within the sheath, and
   a frosted finish on the external surface of said sheath.

2. The intubating stylet of claim 1 wherein said tubular sheath is made of plasticized polyvinyl chloride resin having a Shore A durometer of between about 70 to 85.

3. The intubating stylet of claim 1 wherein said metal rod is formed of aluminum metal.

4. The intubating stylet of claim 3 wherein said aluminum is type 1100–0.

* * * * *